United States Patent [19]

Ayorinde et al.

[11] Patent Number: 5,491,244

[45] Date of Patent: Feb. 13, 1996

[54] ACRYLATE ESTER

[75] Inventors: Folahan O. Ayorinde, Upper Marlboro; Mahmoud Hassan, Silver Spring, both of Md.

[73] Assignee: Howard University, Washington, D.C.

[21] Appl. No.: 476,983

[22] Filed: Jun. 7, 1995

Related U.S. Application Data

[62] Division of Ser. No. 250,213, May 27, 1994.

[51] Int. Cl.⁶ .................................................. C07D 303/16
[52] U.S. Cl. .......................................................... 549/561
[58] Field of Search ............................................. 549/561

[56] References Cited

U.S. PATENT DOCUMENTS

| | | | |
|---|---|---|---|
| 3,584,015 | 6/1971 | Lee et al. | 260/348 A |
| 4,311,645 | 1/1982 | Rosenberger | 260/348.61 |
| 4,874,558 | 10/1989 | Fife et al. | 562/894 |

OTHER PUBLICATIONS

Journal of Polymer Science: Part A, vol. 2, pp. 2385–2400 (1964); *Acrylic Anhydrides and Polymers Derived Therefrom;* Jesse C. H. Hwa, William A. Fleming, and Leon Miller; Research Laboratory, Rohm and Haas Company, Philadelphia, Pennsylvania.

March, J. *Advanced Organic Chemistry* (John Wiley & Sons, New York), p. 355 (1985).

*Primary Examiner*—Mukund J. Shah
*Assistant Examiner*—King L. Wong
*Attorney, Agent, or Firm*—Kenyon & Kenyon

[57] ABSTRACT

The present invention concerns a method for the production of olefin anhydrides, such as acrylic anhydride and methacrylic anhydride, via reactions between an aromatic acid chloride, such as benzoyl chloride, and carboxylate ions of the olefin acid corresponding to the anhydride to be produced. The method of the invention may be conducted without the use of a solvent, catalyst, polymerization inhibitor, or an external source of heat. Moreover the acrylic anhydrides of the invention can be used to produce high yields of acrylate esters by means of room-temperature reactions, without mineral acid catalysis.

1 Claim, No Drawings

ACRYLATE ESTER

This is a division of application Ser. No. 08/250,213 filed May 27, 1994 pending.

FIELD OF THE INVENTION:

This invention relates to a process in which olefin acid anhydrides are produced by the reaction of an acid chloride and a carboxylate ion corresponding to the olefin acid anhydride to be produced. The process may be conducted without the use of an external source of heat, without catalysts, without polymerization inhibitors and without solvent. This invention also relates to a process wherein acrylic acid anhydride or methacrylic acid anhydride is produced by reacting an aromatic acid chloride with the corresponding carboxylate ion of acrylic anhydride or methacrylic acid anhydride. The above anhydrides can subsequently be reacted with alcohols at room temperature, without the need for any catalyst, to give high yields of the corresponding acrylate esters.

BACKGROUND OF THE INVENTION

Several million pounds of olefin acid esters, particularly acrylate and methacrylate esters, are produced in industry each year for a wide range of applications including paint formulations, lenses, fiber optics, coatings, dental fillings and so forth. These industrial chemical intermediates have been prepared conventionally by Fischer esterification, wherein a mineral acid catalyst is employed. See, e.g., Mitsubishi Rayon Co. Ltd., Japanese patent 58,204,057 (1983). All references cited herein are incorporated by reference unless indicated otherwise. In the case where acrylate esters are prepared using the Fischer procedure, a danger of explosions exists due to rapid polymerization of the product. Another drawback of the Fischer procedure is that the procedure does not lend itself to reaction systems that contain acid-sensitive groups.

Other methods that are used to produce esters are generally based on the reaction of an acid chloride with an alcohol in the presence of a hydrochloric acid scavenger such as pyridine. See, e.g., MacCabe, J. F. and H. J. Wilson, *J. of Oral Rehabilitation,* 1:335 (1974); Sakaguchi, R. L., M. C. R. B. Peters, S. R. Nelson, W. H. Douglas and H. W. Poort, *J. Dent.,* 20:178 (1992); and Kimura, H., F. Teraoka and T. Saito, *J. Osaka Univ. Dent. Sch.,* 23:51-8 (1983). However, for the synthesis of acrylates, such methods require the use of acryloyl chloride or methacryloyl chloride which are lachrimators (irritating to skin, eyes, and mucous membranes), in addition to being toxic.

The reaction of an alcohol with an anhydride is yet another method of synthesizing esters. While methacrylic anhydride is commercially available, acrylic anhydride is not. Moreover, the preparation of acrylic anhydride, as in the case of most anhydrides, generally requires the reaction of the acrylic acid, or carboxylate ion of the acid, with acryloyl chloride. In an investigation concerning the polymerization of acrylic anhydrides, Hwa and coworkers synthesized acrylic anhydride, methacrylic anhydride, acrylic-methacrylic anhydride and acrylic-propionic anhydride by reaction of carboxylate salts with acryloyl chloride, methacryloyl chloride, acryloyl chloride and propionyl chloride respectively. Hwa, J. C. H., W. A. Fleming and L. Miller, *Journal of Polymer Science: Part A,* Vol. 2, pp. 2385–2400 (1964). In these syntheses, benzene was used as solvent and methylene anthrone (a polymerization inhibitor) was added. These investigators made similar, but unsuccessful, attempts to synthesize the following mixed anhydrides: methacrylic-isobutyric anhydride, dimethacrylic-fumaric anhydride, methacrylic-benzoic anhydride and methacrylic-cinnamic anhydride. In these reactions, the authors reported either symmetrical products, or mixtures of symmetrical and non-symmetrical products. Disadvantages of the above method include the health hazards associated with acryloyl chloride and benzene, which mitigate against its use in the synthesis of acrylic anhydride.

SUMMARY OF THE INVENTION

In view of the above and other deficiencies in the prior art, there is presently a need for a novel and viable synthetic procedure for the production of various symmetrical olefin acid anhydrides that does not require the use of catalysts, inhibitors, solvents, external heat sources or acid chlorides corresponding to the anhydride to be produced. Such anhydrides are useful, for example, in the syntheses of esters that contain acid-sensitive groups.

According to an embodiment of the invention, a process for the substantially simultaneous production of a symmetrical olefin acid anhydride and a symmetrical non-olefin acid anhydride is provided. In this embodiment, a carboxylate ion of an olefin acid is mixed with an acid chloride in a manner such that the carboxylate ion is provided in a stoichiometric excess relative to the acid chloride. As a result, a symmetrical olefin acid anhydride is produced, as well as a symmetrical non-acrylic anhydride. In this embodiment, the acid chloride is preferably selected such that the carboxylate ion of the acid chloride is less reactive as a nucleophile (i.e., less reactive toward a mixed anhydride derived from the olefin acid and the acid chloride) than the carboxylate ion of the olefin acid.

According to another embodiment of the invention, acrylic anhydride and methacrylic anhydride are produced via reactions between an aromatic acid chloride, such as benzoyl chloride, and carboxylate ions of acrylic acid and methacrylic acid, respectively, without the need for a solvent, catalyst, polymerization inhibitor, or an external heat-source.

According to another embodiment of the invention, the above olefin anhydrides are used to produce high yields of olefin acid esters by room-temperature reactions with a variety of alcohols, without the need for mineral acid catalysts.

This invention is advantageous with respect to current technologies in that it results in lower energy consumption, less hazardous reaction conditions, less environmental disposal problems, and greater product yields.

This invention is also advantageous in that acrylic anhydride and methacrylic anhydride can be produced without the use of acryloyl chlorides by simple reactions between acid chlorides and the carboxylate ions of acrylic acid or methacrylic acid.

Another advantage of the present invention is that the resulting acrylic anhydrides can be reacted with a variety of alcohols at room temperature, without mineral acid catalysts, to give high yields of acrylate esters.

Other advantages and embodiments will become apparent to those of skill in the art after viewing the detailed description, materials and methods, examples, and claims to follow. Additional embodiments in the appended claims are also hereby incorporated in this section by reference.

DETAILED DESCRIPTION OF THE INVENTION

According to an embodiment of the invention, a first carboxylate ion of an olefin acid, preferably acrylic acid or methacrylic acid, is provided and mixed with an acid chloride, preferably an aromatic chloride such as benzoyl chloride or o-, p- or m-methylbenzoyl chloride, in the absence of solvent.

Without being held to any particular theory, it is believed that the reaction between the carboxylate ion and the acid chloride proceeds according to the following reaction scheme, hereinafter referred to as reaction scheme I, which is based on the production of acrylic anhydride:

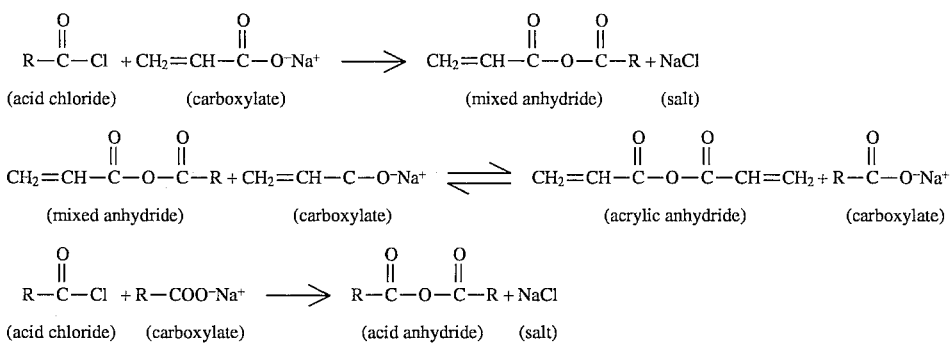

The present inventors have found that the above reaction scheme is unexpectedly advantageous in comparison with prior reaction schemes, because it does not require the use of catalysts, polymerization inhibitors, solvents, external heat sources or the use of acryloyl chlorides.

Preferred symmetrical olefin acid anhydrides for the practice of the invention include acrylic anhydride and methacrylic anhydride.

The carboxylate ions of the olefin acids used to form the corresponding symmetrical olefin acid anhydrides in the above reaction scheme can be produced by the reaction of the olefin acid with a suitable base such as sodium hydroxide and potassium hydroxide. For example, carboxylate ions of acrylic acid and methacrylic acid are easily obtained by reacting sodium hydroxide with acrylic acid and methacrylic acid to form sodium acrylate and sodium methacrylate, respectively. Similarly, potassium acrylate and potassium methacrylate can be prepared upon reaction of acrylic acid and methacrylic acid, respectively, with potassium hydroxide. The potassium salts appear to react in the same manner as the corresponding sodium salts, indicating that the counter-ion of the carboxylate salt appears to have little or no effect on the outcome of the reaction between the carboxylate ion and the acid chloride and/or the mixed anhydride.

The acid chlorides for use in the present invention preferably meet several criteria. First, the acid chloride is preferably less toxic and expensive than acryloyl chloride. Second, the acid chloride preferably forms a non-olefin anhydride that is easily separated from the olefin anhydride produced. Moreover, in order to produce a good yield of olefin anhydride (particularly acrylic or methacrylic-anhydride), the selected acid chloride also preferably meets the following criteria: 1) the acid chloride is desirably less reactive with carboxylate ion of the olefin acid than is the intermediate mixed anhydride: 2) the carboxylate ion of the acid chloride is desirably less reactive as a nucleophilic agent than the carboxylate ion of the olefin acid; and 3) the non-olefin anhydride product is desirably quite unreactive towards carboxylate ions. Finally, the carboxylate ion of the olefin acid is preferably provided in a slight excess relative to the acid chloride or acid anhydride in order to shift the equilibrium represented by the second equation in the above reaction scheme to favor the formation of the desired symmetrical anhydrides.

The preferred acid chlorides for use in the present invention are aromatic acid chlorides such as benzoyl chloride or o-, p- or m-methylbenzoyl chloride, with benzoyl chloride being most preferred. Of course, those of skill in the art will be able to determine other desirable acid chlorides.

As an example, in developing the above novel synthetic route in connection with acrylic anhydride and methacrylic anhydride, several acid chlorides were examined that are not only less expensive, but also less hazardous, than acryloyl chloride.

As seen below, benzoyl chloride, acetyl chloride and pivaloyl chloride were tested for use in the present invention. The best results were obtained with benzoyl chloride, which provided a yield of the acrylic anhydride of 77.2%. Acetyl chloride gave a less preferred product mixture that comprised 50% mixed anhydride, 25% acetic anhydride and 25% acrylic anhydride; the pivaloyl chloride reaction also gave a less preferred product mixture that comprised 50% mixed anhydride, 30% pivaloyl anhydride and 20% acrylic anhydride, based on gas chromatographic analysis. Benzoyl chloride is also more preferred than acetyl chloride and trimethyacetyl (pivaloyl) chloride, because the benzoyl chloride reaction yields benzoic anhydride which has a much greater boiling point than acrylic anhydride, facilitating the separation of the acrylic anhydride.

As noted above, the most preferred results are obtained (i.e., the products consisted almost exclusively of symmetrical anhydrides) when the carboxylate salts are added in slight stoichiometric excess with respect to the acid chloride. For example, when benzoyl chloride is used in excess in the synthesis of acrylic anhydride, a complex product mixture containing acrylic anhydride, benzoic anhydride, unreacted benzoyl chloride and the mixed anhydride is formed. In this case, gas chromatographic analysis showed that the mixed anhydride was the major product.

Moreover, in the case of benzoyl chloride, the resulting mixed anhydride is more reactive than benzoyl chloride. Thus, the carboxylate ion of acrylic acid preferentially reacts with the mixed anhydride to give acrylic anhydride and the benzoate ion, which subsequently reacts with unreacted benzoyl chloride to give benzoic anhydride, according to reaction scheme I.

Acetyl chloride and trimethylacetyl (pivaloyl) chloride, on the other hand, lead to lower yields of acrylic anhydride and higher yield of the mixed anhydride. In these cases the resulting mixed anhydrides are less reactive than the acid chlorides. Hence, the carboxylate ion of acrylic acid preferentially reacts with the acid chlorides rather than the mixed anhydrides according to reaction scheme I, leading to higher yields of the mixed anhydride.

Unlike prior art methods, the process of the present invention may be conducted in the absence of solvents. This is advantageous, because there is no need to separate solvent from the reaction products after the reaction is complete. This is also advantageous, because reactions in which benzoyl chloride is used in the presence of solvents results in the formation of complex mixtures that include the desired products, mixed anhydrides, unreacted starting materials and unidentified products. Those solvents tested include dichloromethane, acetone, hexane and acrylic acid. In all of these cases, the reaction rates were reduced and, thus, the reaction times were markedly increased. For example, whereas the non-solvent reaction was completed in less than one hour, reaction with hexane lasted at least 20 hours, with the formation of complex product mixture.

According to another embodiment of the invention, the carboxylate ions of the olefin acids are replaced by the olefin acids themselves. This reaction, however, is less preferred because hydrogen chloride gas is generated. Nevertheless, the danger of hydrogen chloride gas can be minimized by using an acid scavenger.

According to another embodiment of the invention, carboxylate ions of olefin acids are reacted with a non-olefin acid anhydride to give an olefinic acid anhydride and carboxylate ions corresponding to the non-olefin acid anhydride. The proposed mechanism for this reaction, hereinafter referred to as reaction scheme II, is as follows:

According to another embodiment of the invention, the olefin acid anhydrides are reacted with alcohols to give high yields of the acrylate esters at room temperature. In particular, acrylic anhydride has been reacted with a series of alcohols ranging from C-1 to C-18 to give high yields of the acrylate esters at room temperature. The synthesis of acrylate esters by the reaction of alcohols with acrylic anhydride were found to proceed essentially to completion at room temperature to yield only the desired acrylate esters. The following mechanism is proposed for this reaction:

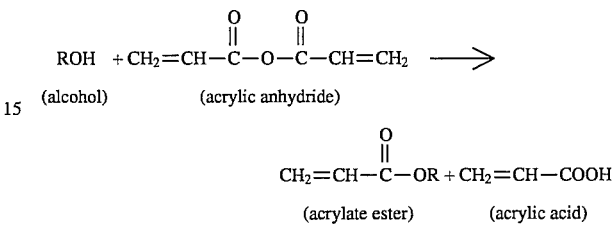

No significant competing reactions were observed, such as the Michael addition reactions that often accompany the production of acrylate esters under reflux conditions. The following are representative of this embodiment: (1) the reaction of n-butyl alcohol with acrylic anhydride was completed in 3.5 hours and yielded 91.2% of n-butyl acrylate; (2) the reaction of n-octyl alcohol with acrylic anhydride was completed in 4 hours to obtain an 81.3% yield of n-octyl acrylate; and (3) the reaction of cis-12,13-epoxy-cis-9-octadecenol with acrylic anhydride was completed in 55 hours to give an 88.4% yield of cis-12, 13-epoxy-cis-9-octadecenyl acrylate.

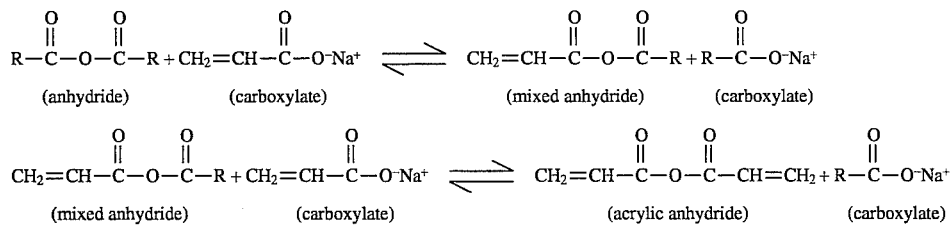

In this scheme, similar mechanistic requirements and reaction conditions should be considered as compared to reaction scheme I. For example, the mixed anhydride is preferably more reactive with the carboxylate ion than the starting acid anhydride. Additional mechanistic requirements dictate that the carboxylate ion from the starting acid anhydride should be less reactive than the carboxylate ion from acrylic acid in order to prevent the retro conversion of acrylic anhydride to the mixed anhydride. Thus, as in the case of the acid chloride route, the choice of the starting acid anhydride determines preferential formation of acrylic anhydride or mixed anhydride. In this case, a mixed anhydride and acrylic anhydride are formed in addition to unreacted starting acid anhydride, thereby posing a greater separation problem. This was demonstrated by the use of acetic anhydride, butyric anhydride and methacrylic anhydride. For these reactions, the mixed anhydrides constitute the major product. Gas chromatographic analyses indicate the ratio of acrylic anhydride to the mixed anhydride to be no better than 1:50. However, addition of alcohols to these reaction mixtures afforded acrylate esters. Hence we concluded that even though synthesis of acrylic anhydride, starting from another anhydride, may not be practicable via this approach, it was possible to produce acrylate esters through this route.

This final case demonstrates the mildness and non-acidic nature of the room-temperature reaction of acrylic anhydride with alcohols, because the acid-sensitive epoxy functionality remains intact. Thus, the present invention constitutes an efficient process for acrylating molecules that contain acid-sensitive groups. The above experiments also suggest a trend in the reaction time of alcohols with acrylic anhydride, in which longer carbon-chain alcohols require longer reaction times. This trend is probably due to the greater steric effects associated with the bigger molecules.

The cis-12,13-epoxy-cis-9-octadecenyl acrylate (i.e.,

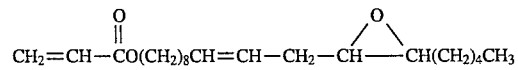

produced in this invention is a novel acrylate ester which is useful in polymeric systems. Moreover, the above ester is expected to have applications in various polymeric systems that require the inclusion of biodegradable components. The epoxy alcohol used in the synthesis of cis-12,13-epoxy-cis-9-octadecenyl acrylate is derived from the lithium aluminum hydride reduction of vernonia oil, a vegetable oil available from International Flora Technologies, Apache Junction, Ariz. 85220. For an example of how to produce the epoxy alcohol, see, for example, Kent Bryant, Howard University Ph.D. dissertation, August 1993.

It should be noted that the acrylic anhydride was isolated prior to reaction with the alcohols in the above cases in order to simplify the isolation and/or purification of the resulting acrylate esters. If so desired, the acrylate esters can be produced without a purification step by adding the alcohol directly to reaction mixture resulting from the acrylic anhydride synthesis.

MATERIAL AND METHODS

The process of the present invention is very simple, utilizing only reagents such as sodium hydroxide, olefin acids, such as acrylic acid and methacrylic acid, and an acid chloride such as benzoyl chloride. The reactions and products were monitored with a Finnigan gas chromatograph (GC model 9611) equipped with a splitless injector and interfaced with a Finnigan MAT 4500 automated mass spectrometer having a Superincos data system. Monitoring was also conducted using a Hewlett Packard gas chromatograph (5890 Series II) coupled with a Hewlett Packard 5971A mass spectrometer. Both mass spectrometers were operated in the electron impact (EI) mode with electron energy of 70 eV. High resolution capillary gas chromatography was conducted on both on both gas chromatographs using a Supelco fused silica SPB-1 (30 m, 0.32 mm I.D., 0.25 um film) column. The oven temperature was programmed over 50° C. to 300° C. at 12° C./min. Helium was used as carrier gas with a head pressure of 10 psi for the Finnigan gas chromatograph and 0.2 psi for the Hewlett Packard gas chromatograph. Perkin Elmer 983G and Perkin Elmer 1600 FT-Infrared Spectrophotometers were used to obtain infrared (IR) spectra. Liquid samples were run neat. Solid samples were run using KBr. Nuclear magnetic resonance spectra for both protons and carbon-13 were recorded on a GE-NMR QE-300 MHz spectrometer with chloroform-d ($CDCl_3$) as solvent and internal standard. Melting points (m.p.) were obtained on a mel-temp II capillary melting point apparatus while boiling points (b.p.) were determined using micro-boiling tube apparatus. The present invention can be more fully understood from the Examples below.

EXAMPLES

Example 1: Preparation of Sodium Acrylate 12.01 g (0.3003 mol) sodium hydroxide and 10 ml water were added to a 50-ml Erlenmayer flask equipped with a magnetic stirring bar, and the mixture was stirred to dissolution. The sodium hydroxide solution was then carefully added to a 250-ml beaker containing 28.03 g (0.3893 mol) acrylic acid (exothermic reaction), with continuous stirring. The mixture was allowed to cool, 50 ml of acetone were added, and the precipitate vacuum filtered. The wet sodium acrylate was first air dried and subsequently dried in an oven at 55°–60° C. for 12–15 hours to obtain 27.31 g (96.8% yield) of sodium acrylate. A similar procedure was used for the preparation of potassium acrylate, except that potassium hydroxide was used instead of sodium hydroxide.

Example 2: Preparation of Sodium Methacrylate

A 12.23 g (0.3058 mol) sample of sodium hydroxide was placed in a 50-ml Erlenmayer flask equipped with 10 ml water and a magnetic stirring bar, and the mixture was stirred to dissolution. The sodium hydroxide solution was then poured into a 250-ml beaker containing 30.70 g (0.3570 mol) methacrylic acid (exothermic reaction) with constant stirring. The mixture was allowed to cool, 50 ml of acetone were added, and the precipitate vacuum filtered. The recovered carboxylate salt was first allowed to air dry under a hood, and then dried in an oven at 55°–60° C. for 12–15 hours to afford 30.43 g (92.2% yield) of sodium methacrylate.

Example 3: Synthesis of Acrylic Anhydride from Benzoyl Chloride

A 60.09 g (0.4277 mol) sample of benzoyl chloride was added to a 500-ml round-bottomed flask equipped with a magnetic stirring bar. 30.02 g (0.3194 mol) of sodium acrylate were then added and stirred for 30 minutes, after which another 15.21 g (0.1618 mol) portion of sodium acrylate was added in one portion, and stirring was continued for additional 30 minutes under the same conditions. The mixture was vacuum filtered neat to obtain 56.41 g of crude product. It should be noted that a more efficient vacuum filtration system would increase the percent recovery of the crude products. Acrylic anhydride was distilled at 65°–67° C. and about 5–10 mm Hg pressure to afford 20.84 g (77.3% yield). MS data: m/z 98 (<2,M-CO), 55 (100, $CH_2=CH-CO^+$). IR data: 1794.5 & 1730.2 $cm^{-1}$ C=O, 16.28.9 $cm^{-1}$ C=C. P-NMR data: vinyl protons all giving doublets of doublets at 6,587, 6,591 & 6.531, 6.535 ppm; 6.227, 6.193 & 6.171, 6.137 ppm; and 6.092, 6,087 & 6.057, 6.053 ppm respectively. C-13 NMR data: 162 ppm (C=O), 135 ppm & 128 ppm (C=C). The residual material in the distillation flask was found to be 31.68 g benzoic anhydride (65.6% yield).

Example 4: Synthesis of Acrylic Anhydride from Acetyl Chloride 20.06 g (0.2581 mol) acetyl chloride was transferred to a 100-ml round-bottom flask equipped with a magnetic stirring bar. Sodium acrylate (0.3205 mol) was then added in three portions: first a 10.00 g portion, and then a 10.10 g portion after 10 minutes with continuous stirring, and finally a 10.03 g portion after another 10 minutes. The reaction was allowed to proceed for 1 hour with constant stirring at room temperature. In order to facilitate subsequent filtration and reduce loss of products, 10 ml methylene chloride was added and the mixture was then vacuum filtered. The filter cake was flushed with another 10-ml portion of methylene chloride, which was then stripped to afford a product mixture of 24.2 g (90.2% yield based on the mixed anhydride) containing acetic anhydride, mixed anhydride and acrylic anhydride in an approximate ratio of 1:2:1 respectively according the GC peak areas. MS data: mixed anhydride; 115 (<1, M+1), 99 (<1, M-$CH_3$), 86 (2.2, M-CO), 55 (57, $CH_2=CH-CO^+$), 43 (100, $CH_3CO$).

Example 5: Synthesis of Methacrylic Anhydride from Benzoyl Chloride

A 25.26 g (0.1798 mol) sample of benzoyl chloride was transferred to a 100-ml round-bottomed flask containing a magnetic stirring bar. 12.12 g (0.1122 mol) sodium methacrylate were then added. After 15 minutes, another 10.50 g (0.0972 mol) portion of sodium methacrylate was added and stirring continued at room temperature for an additional 45 minutes. The mixture was then vacuum filtered to obtain 29.27 g of crude product. The methacrylic anhydride was distilled at 72°–74° C. at 5–10 mm Hg to afford 5.95 g (43% yield). The low yield was attributed to material loss due to filtration. MS data (m/z): 126 (<1, M-CO), 69 (78, $CH_2=C(CH_3)CO^+$), 41 (100, $CH_2=C(CH_3)^+$).

Example 6: Synthesis of N-Butyl Acrylate 3.00 g (0.0238 mol) acrylic anhydride and 2.48 g (0.0335 mol) n-butyl alcohol were transferred to a 50-ml round-bottomed flask, equipped with a magnetic stirring bar. The mixture was stirred for 3–3.5 hours continuously at room temperature.

The reaction was terminated by the addition of 10 ml water and 5 ml methylene chloride, and the aqueous portion was separated. Another 10 ml portion of water was added to extract the excess alcohol and acrylic acid. The organic portion was further extracted with cold 10 ml 1M sodium hydroxide solution. Methylene chloride was distilled off to afford 2.78 g n-butyl acrylate (91.2% yield) with a GC purity of 99+% and a boiling point of 143°–144° C. (inhibited with 400 ppm 4-methoxyphenol) lit. bp. 145° C. MS data: m/z 129 (<1, M+1), 113 (<2, M-$CH_3$), 99 (3, M–$CH=CH_2$), 73 (70, M–O=C–CH=$CH_2$), 55 (100, $CH_2=CH-C=O^+$).

Example 7: Synthesis of N-octyl Acrylate

A 3.00 g (0.0238 mol) sample of acrylic anhydride was transferred to a 50-ml round-bottomed flask that was equipped with a magnetic stirring bar. 4.60 g (0.0354 mol) of n-octyl alcohol were then added. The mixture was then stirred continuously at room temperature for 3.5–4 hours.

The reaction was stopped by addition of 10 ml water, followed by 5 ml methylene chloride, and the aqueous portion was separated. The methylene chloride solution was extracted with another 10 ml portion of water, followed by 10 ml of cold 1M sodium hydroxide. The methylene chloride was evaporated to afford a 5.01 g crude product containing the desired n-octyl acrylate and excess n-octyl alcohol. The n-octyl acrylate was isolated and characterized as described below.

Example 8: Isolation and Characterization of N-Octyl Acrylate

A glass chromatographic column (84.0 cm long with an internal diameter of 2.0 cm), was first packed with glass wool (2.0 cm deep), followed by about 20 g activated neutral alumina (Aldrich Chemical Co., Milwaukee, Wis. 53233, USA). The crude product mixture from Example 7 was transferred unto the column and allowed to diffuse into the stationary phase. Hexane (80 ml) was used to elute 3.56 g n-octyl acrylate (81.3% yield), with a GC purity of 99+% and a boiling point of 212° C. (inhibited with 600 ppm of 4-methoxyphenol). MS data: 185 (<1, M+1), 169 (<1, M-$CH_3$), 155 (<1, M-$CH_2CH_3$), 55 (100, $CH_2=CH-C=O^+$); IR data (cm$^{-1}$): 1720 C=O, 1637.4 C=C; C-13 NMR data (ppm): 166.20 C=O, 130.16 and 128.68 vinyl carbons, 64.63 carbon alpha to the oxygen atom, 31.73, 29.16, 29.12, 28.60, 25.89, 22.57 for the methylene groups, 13.97 for the methyl group.

Example 9: Synthesis of cis-12,13-Epoxy-cis-9 Octadecenyl Acrylate

To a 100-ml round bottomed flask was transferred 3.03 g (0.0241 mol) acrylic anhydride and then 1.50 g (0.0053 mol) cis-12, 13-epoxy-cis-9-octadecenol, while stirring continuously with a magnetic stirring bar for 55–60 hours at room temperature. A 5-ml portion of hexane and a 10-ml portion of water were added and the aqueous portion was separated. Further extraction of the hexane layer was carried out with another 10 ml portion of water and then with a 10 ml portion of saturated sodium bicarbonate solution (x 2) to afford 1.58 g (88.4% yield) of cis-12, 13-epoxy-cis-9-octadecenyl acrylate. MS data: m/z 336 (1, M$^+$), 293 (1, M- $CH_2CH_2CH_3$), 265 (1, M-OOCCH=$CH_2$), 223 (2, M- CH-CH ($CH_2)_4CH_3$), 113 (28, ($CH_2)_3$OOCCH=$CH_2$), 99 (60, $CH_2CH_2$OOCCH=$CH_2$), 55 (100, $CH_2$=CHCOO$^+$). C-13 NMR data (ppm): 166.14 C=O; 132.44, 130.21, 128.55 and 123.82 for vinyl carbons; 64.52 for the carbon alpha to the oxygen; 57.05 and 56.39 for the epoxy carbons.

We claim:

1. A chemical compound of the formula:

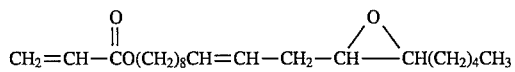

* * * * *

UNITED STATES PATENT AND TRADEMARK OFFICE
CERTIFICATE OF CORRECTION

PATENT NO. : 5,491,244
DATED : 13 February 1996
INVENTOR(S) : Folahan O. AYORINDE et al.

It is certified that error appears in the above-indentified patent and that said Letters Patent is hereby corrected as shown below:

| Column | Line | |
|---|---|---|
| 6 | 25 | Change "n-butyl" to --n-butyl--. |
| 6 | 26 | Change "n-butyl" to --n-butyl--. |
| 6 | 27 | Change "n-octyl" to --n-octyl--. |
| 6 | 29 | Change "n-octyl" to --n-octyl--; change "cis-12,13-epoxy-" to --cis-12,13-epoxy-- |
| 6 | 30 | Change "cis-9-octadecenol" to --cis-9-octadecenol--. |
| 6 | 31 | Change "cis-12, 13-epoxy-cis-9-" to --cis-12,13-epoxy-cis-9- --. |
| 6 | 54 | Change "cis-12,13-epoxy-cis-9-octadecenyl" to --cis-12,13-epoxy-cis-9-octadecenyl--. |

UNITED STATES PATENT AND TRADEMARK OFFICE
CERTIFICATE OF CORRECTION

PATENT NO. : 5,491,244
DATED : 13 February 1996
INVENTOR(S) : Folahan O. AYORINDE et al.

It is certified that error appears in the above-indentified patent and that said Letters Patent is hereby corrected as shown below:

| Column | Line | |
|---|---|---|
| 6 | 63 | Change "cis-12,13-epoxy-cis-" to --cis-12,13-epoxy-cis- --. |
| 9 | 28 | Change "n-octyl" to --n-octyl--. |
| 9 | 36 | Change "n-octyl" to --n-octyl-- (both occurrences). |
| 9 | 37 | Change "n-octyl" to --n-octyl--. |
| 10 | 5 | Change "n-octyl" to --n-octyl--. |

UNITED STATES PATENT AND TRADEMARK OFFICE
CERTIFICATE OF CORRECTION

PATENT NO. : 5,491,244
DATED : 13 February 1996
INVENTOR(S) : Folahan O. AYORINDE et al.

It is certified that error appears in the above-indentified patent and that said Letters Patent is hereby corrected as shown below:

| Column | Line | |
|---|---|---|
| 10 | 22 | Change "cis-12, 13-epoxy-cis-9-octadecenol" to --*cis*-12,13-epoxy-*cis*-9-octadecenol--. |
| 10 | 29 | Change "cis-12, 13-epoxy-cis-9-octadecenol" to --*cis*-12,13-epoxy-*cis*-9-octadecenol--. |

Signed and Sealed this

Twenty-seventh Day of August, 1996

Attest:

BRUCE LEHMAN

Attesting Officer    Commissioner of Patents and Trademarks